(12) United States Patent
Harris et al.

(10) Patent No.: US 7,534,875 B2
(45) Date of Patent: May 19, 2009

(54) COMPOSITIONS FOR GLIOMA CLASSIFICATION

(75) Inventors: Cole Harris, Albuquerque, NM (US); Lisa Davis, Albuquerque, NM (US)

(73) Assignee: Exagen Diagnostics, Inc., Albuquerque, NM (US)

( * ) Notice: Subject to any disclaimer, the term of this patent is extended or adjusted under 35 U.S.C. 154(b) by 231 days.

(21) Appl. No.: 10/981,277

(22) Filed: Nov. 3, 2004

(65) Prior Publication Data

US 2005/0181389 A1 Aug. 18, 2005

Related U.S. Application Data

(60) Provisional application No. 60/516,817, filed on Nov. 3, 2003.

(51) Int. Cl.
  C07H 21/02 (2006.01)
  C07H 21/04 (2006.01)
  C12Q 1/68 (2006.01)

(52) U.S. Cl. .................. 536/23.5; 536/23.1; 536/24.31; 536/24.33; 435/6

(58) Field of Classification Search ........................ None
See application file for complete search history.

(56) References Cited

U.S. PATENT DOCUMENTS

| 5,750,340 | A | 5/1998 | Kim et al. |
| 6,022,689 | A | 2/2000 | Sarto et al. |
| 6,344,316 | B1 * | 2/2002 | Lockhart et al. ............... 506/9 |
| 6,664,057 | B2 | 12/2003 | Albertson et al. |
| 6,706,867 | B1 * | 3/2004 | Lorenz ....................... 536/23.1 |
| 2003/0187584 | A1 | 10/2003 | Harris et al. |

FOREIGN PATENT DOCUMENTS

| WO | WO 96/17958 | 6/1996 |
| WO | 2003083760 | 10/2003 |

OTHER PUBLICATIONS

Affymetrix Human Genome U95Av2 Array. Affymetrix Product Catalog for GeneChip Human Genome 95 Set, 2000.*
Coleman. Drug Discovery Today. 2003. 8: 233-235.*
Liu et al. Clinical Immunology. 2004. 112: 225-230.*
Nutt, et al., (2003), Cancer Research, "Gene expression-based classification of malignant gliomas correlates better with survival than histological classification", vol. 63, pp. 1602-1607.
Hyman, et al., (2002), Cancer Res., "Impact of DNA amplification on gene expression patterns in breast cancer", vol. 62(21), pp. 6240-6245.
Hanash, et al., (2002), Proteomics, "integrating cancer genomics and proteomics in the post-genome era", vol. 2(1), pp. 69-75.
Kim, et al., (2002), Molecular cancer therapeutics, "Identification of combination gene sets for glioma classification", vol. 1(13), pp. 1229-1236.
Pollack, et al., (2002), Proc. Natl. Acad. Sci. USA, "Microarray analysis reveals a major direct role of DNA copy number alteration in the transcriptional program of human gliomas", vol. 99(20), pp. 12963-12968.
Pollack, et al., (1999), Nature Genetics, "Genome-wide analysis of DNA copy-number changes using cDNA microarrays", vol. 23(1), pp. 41-46.
Crawley, et al., (2002), Genome Biol., "Identification of frequent cytogenetic aberrations in hepatocellular carcinoma using gene-expression microarray data", vol. 3(12), pp. 1-8.
Barlund, et al., (2000), Cancer Res. "Multiple Genes at 17q23 Undergo Amplification and Overexpression in Breast Cancer", vol. 60(19), pp. 5340-5344.
Kauraniemi, et al., (2001), Cancer Res., "New Amplified and Highly Expressed Genes Discovered in the ERBB2 Amplicon in Breast Cancer by cDNA Microarrays", vol. 61(22), pp. 8235-8240.
Monni, et al., (2001), Proc. Natl. Acad. Sci., "Comprehensive Copy Number and Gene Expression Profiling of the 17q23 Amplicon in Human Breast Cancer", vol. 98(10), pp. 5711-5716.
Strauss-Soukup, (1997), Biochemistry, "Effects of Neutralization Pattern and Sterochemistry on DNA Bending By Methylphosphonate Substitutions" vol. 36, pp. 8692-8698.
Milligan (1993), J. Med. Chem., "Current Concepts in Antisense Drug Design", vol. 36, pp. 1923-1937.
Pearson, et al., (1983), J. Chrom, "High-Performance Anion-Exchange Chromatography of Oligonucleotides", vol. 255, pp. 137-149.
Pastinen, et al., (1997), Genome Res., "Minisequencing: A Specific Tool for DNA Analysis and Diagnostics on Oligonucleotide Arrays", vol. 7, pp. 606-614.
Wan, et al., (1996), Nature Biotechnology, "Cloning Differentially Expressed mRNAs", vol. 14, p. 1685-1691.
Chee, et al., (1995), Science, "Accessing Genetic Information with High-Density DNA Arrays", vol. 274, p. 610.
Kros, et al., (1999), J. Pathol., "Genetic aberrations in oligodendroglial tumors: an analysis using comparative genomic hybridization (CGH)", vol. 188(3), pp. 282-288.
Maruno, et al., (1999), Cancer Lett., "Chromosomal aberrations detected by comparative genomic hybridization (CGH) in human astrocytic tumors", vol. 135(1), pp. 61-66.
Nigro, et al., (2005), Cancer Research, "Integrated Array-Comparative Genomic Hybridization and Expression Array Profiles Identify Clinically relevant Molecular Subtypes of Glioblastoma", vol. 65, pp. 1678-1686.
Progenetix CGH online database. Baudis M., (2000-2003); www.progenetix.net.

(Continued)

*Primary Examiner*—Carla Myers
(74) *Attorney, Agent, or Firm*—McDonnell Boehnen Hulbert & Berghoff LLP; David S. Harper

(57) ABSTRACT

The present invention provides novel compositions and their use in classifying gliomas. In a preferred embodiment, the methods are used to discriminate between oligodendroglioma and glioblastoma.

14 Claims, 9 Drawing Sheets

OTHER PUBLICATIONS

Baudis, et al., (2001) Bioinformatics, "Progenetix.net: An online repository for molecular cytogenetic aberration data.", vol. 17 (12), pp. 1228-1229.

Watson, et al., (2001), Cancer Research, "Gene Expression Profiling with Oligonucleotide Microarrays Distinguishes World Health Organization Grade of Oligonucleotides", vol. 61, pp. 1825-1829.

* cited by examiner

Figure 1A

| Accession Number | gene name and SEQ ID NO | BAC name | chromosome | begin at bp# | end at bp# | size | BAC SEQ ID NO |
|---|---|---|---|---|---|---|---|
| X68194 | h-Sp1 (SEQ ID NO:1) | RP11-193P05 | 7q22.3 | 105,166,071 | 105,313,293 | 147,223 | (SEQ ID NO:21) |
|  |  | RP11-532G04 | 7q22.3 | 105,210,207 | 105,362,088 | 151,882 | (SEQ ID NO:22) |
|  |  |  |  |  |  |  |  |
| D80012 | KIAA0190 (SEQ ID NO:2) | RP11-339O21 | 16q24.1 | 84,378,486 | 84,573,849 | 195,364 | (SEQ ID NO:23) |
|  |  | RP11-80H06 | 16q24.1 | 84,400,522 | 84,560,725 | 160,204 | (SEQ ID NO:24) |
|  |  | RP11-816N18 | 16q24.1 | 84,411,033 | 84,584,732 | 173,700 | (SEQ ID NO:25) |
| X69490 | titin (SEQ ID NO:3) | RP11-65L03 | 2q31.2 | 179,222,165 | 179,394,989 | 172,825 | (SEQ ID NO:26) |
|  |  | RP11-702K16 | 2q31.2 | 179,315,141 | 179,497,648 | 182,508 | (SEQ ID NO:27) |
|  |  |  |  |  |  |  |  |
| AL050050 | DKFZp566D133 (SEQ ID NO:4) | RP11-624P12 | 9q31.2 | 101,698,606 | 101,859,415 | 160,810 | (SEQ ID NO:28) |
|  |  | RP11-556N18 | 9q31.2 | 101,720,729 | 101,900,415 | 179,687 | (SEQ ID NO:29) |
|  |  | RP11-355C03 | 14q13.2 | 33,940,954 | 34,096,525 | 155,572 | (SEQ ID NO:30) |
|  |  |  |  |  |  |  |  |
| Z35491 | GCHRAP (SEQ ID NO:5) | RP11-126M06 | 9p21-p13 | 33,172,137 | 33,355,182 | 183,046 | (SEQ ID NO:31) |
|  |  |  |  |  |  |  |  |

Figure 1B

| | | | | | | |
|---|---|---|---|---|---|---|
| AB029003 | KIAA1080 (SEQ ID NO:6) | RP11-29K03 | 16p12.2 | 23,343,152 | 23,508,690 | 165,539 (SEQ ID NO:32) |
| D87343 | DCRA (SEQ ID NO:7) | RP11-70N15 | 21q22.13 | 37,429,095 | 37,579,576 | 150,482 (SEQ ID NO:33) |
| | | RP11-348K16 | 21q22.13 | 37,454,954 | 37,631,049 | 176,096 (SEQ ID NO:34) |
| X17644 | GST1 (SEQ ID NO:8) | RP11-634H03 | 16p13.13 | 11,906,946 | 12,073,481 | 166,536 (SEQ ID NO:35) |
| | | CTD-2380E14 | 16p13.13 | 11,840,607 | 11,991,131 | 150,525 (SEQ ID NO:36) |
| D13642 | KIAA0017 (SEQ ID NO:9) | RP11-6M02 | 16q22.1 | 70,265,390 | 70,415,708 | 150,319 (SEQ ID NO:37) |
| M80244 | E16 (SEQ ID NO:10) | RP11-389M10 | 16q24.2 | 87,489,494 | 87,670,772 | 181,279 (SEQ ID NO:38) |
| | | RP11-53P23 | 16q24.2 | 87,565,332 | 87,689,927 | 124,596 (SEQ ID NO:39) |
| | | CTD-2195G01 | 16q24.2 | 87,587,950 | 87,741,140 | 153,191 (SEQ ID NO:40) |
| | | RP11-280O07 | 16q24.2 | 87,600,268 | 87,753,011 | 152,744 (SEQ ID NO:41) |
| M63175 | AMFR (SEQ ID NO:11) | RP11-598M09 | 16q12.2 | 56,027,976 | 56,215,372 | 187,397 (SEQ ID NO:42) |
| | | RP11-413H22 | 16q12.2 | 56,075,110 | 56,268,183 | 193,074 (SEQ ID NO:43) |

Figure 1C

| | | | | | | |
|---|---|---|---|---|---|---|
| AJ009771 | RING (SEQ ID NO:12) | RP11-422O02 | 15q24.1 | 70,413,542 | 70,585,384 | 171,843 (SEQ ID NO:44) |
| | | RP11-612A09 | 15q24.1 | 70,333,553 | 70,521,721 | 188,169 (SEQ ID NO:45) |
| AB028985 | KIAA1062 (SEQ ID NO:13) | RP11-466K05 | 9q34.3 | 133,220,670 | 133,371,170 | 150,501 (SEQ ID NO:46) |
| | | RP11-229P13 | 9q34.3 | 133,232,112 | 133,391,761 | 159,650 (SEQ ID NO:47) |
| AB028944 | KIAA1021 (SEQ ID NO:14) | RP11-708D05 | 13q34 | 112,452,696 | 112,628,951 | 176,256 (SEQ ID NO:48) |
| M81118 | ADH5CHI (SEQ ID NO:15) | RP11-571L19 | 4q23 | 100,232,660 | 100,439,398 | 206,739 (SEQ ID NO:49) |
| | | RP11-603F22 | 4q23 | 100,347,459 | 100,497,895 | 150,437 (SEQ ID NO:50) |
| AF070596 | 24796 (SEQ ID NO:16) | RP11-768I19 | 16p12.3 | 20,963,245 | 21,159,395 | 196,151 (SEQ ID NO:51) |
| | | RP11-470O13 | 16p12.3 | 21,007,478 | 21,157,775 | 150,298 (SEQ ID NO:52) |
| | | RP11-480G09 | 16p12.3 -12 | 21,067,644 | 21,232,553 | 164,910 (SEQ ID NO:53) |
| AB018290 | KIAA0747 (SEQ ID NO:17) | CTD-2291O12 | 12q13.2 | 56,229,559 | 56,332,949 | 103,391 (SEQ ID NO:54) |

Figure 1D

| AL050025 | DKFZp564D066 (SEQ ID NO:18) | RP11-417N10 | 16q22.2 | 71,481,584 | 71,631,858 | 150,275 | (SEQ ID NO:55) |
|---|---|---|---|---|---|---|---|
| | | RP11-456N13 | 15q22.2 | 61,089,837 | 61,240,409 | 150,573 | (SEQ ID NO:56) |
| AC002394 | CIT987SKA211C6 (SEQ ID NO:19) | RP11-481A02 | 16p12.3 | 20,749,100 | 20,961,192 | 212,093 | (SEQ ID NO:19) |
| AB011170 | KIAA0598 (SEQ ID NO:20) | RP11-47G11 | 10q26.13 | 125,741,771 | 125,891,011 | 149,241 | (SEQ ID NO:57) |

Figure 2A    Ranking of 5 reporter set glioma biomarkers

| Probe set rank | A | B | C | D | E | gene expression score % (x 100) correct | cgh score % (x 100) correct | average for ranking combinations |
|---|---|---|---|---|---|---|---|---|
| 1 | X68194 (SEQ ID 1) | D80012 (SEQ ID 2) | X69490 (SEQ ID 3) | Z35491 (SEQ ID 5) | D87343 (SEQ ID 7) | 0.875 | 0.944444 | 0.909722 |
| 2 | D80012 (SEQ ID 2) | X69490 (SEQ ID 3) | Z35491 (SEQ ID 5) | D87343 (SEQ ID 7) | AF070596 (SEQ ID 16): | 0.87013 | 0.944444 | 0.907287 |
| 3 | D80012 (SEQ ID 2) | X69490 (SEQ ID 3) | AL050050 (SEQ ID 4) | Z35491 (SEQ ID 5) | D87343 (SEQ ID 7) | 0.857143 | 0.944444 | 0.900794 |
| 4 | X69490 (SEQ ID 3) | Z35491 (SEQ ID 5) | D87343 (SEQ ID 7) | M63175 (SEQ ID 11) | AF070596 (SEQ ID 16): | 0.847403 | 0.944444 | 0.895924 |
| 5 | D80012 (SEQ ID 2) | X69490 (SEQ ID 3) | Z35491 (SEQ ID 5) | D87343 (SEQ ID 7) | AB028985 (SEQ ID 13) | 0.847403 | 0.944444 | 0.895924 |
| 6 | X68194 (SEQ ID 1) | X69490 (SEQ ID 3) | Z35491 (SEQ ID 5) | D87343 (SEQ ID 7) | M63175 (SEQ ID 11) | 0.847403 | 0.944444 | 0.895924 |
| 7 | X69490 (SEQ ID 3) | Z35491 (SEQ ID 5) | D87343 (SEQ ID 7) | M80244 (SEQ ID 10) | AL050025 (SEQ ID 18) | 0.842532 | 0.944444 | 0.893488 |
| 8 | D80012 (SEQ ID 2) | X69490 (SEQ ID 3) | Z35491 (SEQ ID 5) | D87343 (SEQ ID 7) | AB018290 (SEQ ID 17) | 0.842532 | 0.944444 | 0.893488 |

Figure 2B

|   | | | | | | | |
|---|---|---|---|---|---|---|---|
| 9 | X68194 (SEQ ID 1) | X69490 (SEQ ID 3) | AL050050 (SEQ ID 4) | Z35491 (SEQ ID 5) | D87343 (SEQ ID 7) | 0.839286 | 0.944444 | 0.891865 |
| 10 | X68194 (SEQ ID 1) | X69490 (SEQ ID 3) | Z35491 (SEQ ID 5) | D87343 (SEQ ID 7) | M80244 (SEQ ID 10) | 0.834416 | 0.944444 | 0.88943 |
| 11 | X68194 (SEQ ID 1) | X69490 (SEQ ID 3) | Z35491 (SEQ ID 5) | AB029003 (SEQ ID 6) | D87343 (SEQ ID 7) | 0.832792 | 0.944444 | 0.888618 |
| 12 | D80012 (SEQ ID 2) | X69490 (SEQ ID 3) | Z35491 (SEQ ID 5) | D87343 (SEQ ID 7) | M80244 (SEQ ID 10) | 0.829545 | 0.944444 | 0.886995 |
| 13 | D80012 (SEQ ID 2) | X69490 (SEQ ID 3) | Z35491 (SEQ ID 5) | D87343 (SEQ ID 7) | M63175 (SEQ ID 11) | 0.824675 | 0.944444 | 0.88456 |
| 14 | X69490 (SEQ ID 3) | Z35491 (SEQ ID 5) | D87343 (SEQ ID 7) | AF070596 (SEQ ID 16):: | AB018290 (SEQ ID 17) | 0.824675 | 0.944444 | 0.88456 |
| 15 | X68194 (SEQ ID 1) | X69490 (SEQ ID 3) | Z35491 (SEQ ID 5) | D87343 (SEQ ID 7) | AL050025 (SEQ ID 18) | 0.824675 | 0.944444 | 0.88456 |
| 16 | X69490 (SEQ ID 3) | Z35491 (SEQ ID 5) | D87343 (SEQ ID 7) | AF070596 (SEQ ID 16):: | AL050025 (SEQ ID 18) | 0.824675 | 0.944444 | 0.88456 |
| 17 | X69490 (SEQ ID 3) | Z35491 (SEQ ID 5) | D87343 (SEQ ID 7) | M80244 (SEQ ID 10) | AB018290 (SEQ ID 17) | 0.819805 | 0.944444 | 0.882125 |
| 18 | X69490 (SEQ ID 3) | AL050050 (SEQ ID 4) | Z35491 (SEQ ID 5) | D87343 (SEQ ID 7) | AF070596 (SEQ ID 16):: | 0.816558 | 0.944444 | 0.880501 |
| 19 | X68194 (SEQ ID 1) | X69490 (SEQ ID 3) | Z35491 (SEQ ID 5) | D87343 (SEQ ID 7) | AF070596 (SEQ ID 16):: | 0.816558 | 0.944444 | 0.880501 |

Figure 2C

| | | | | | | | |
|---|---|---|---|---|---|---|---|
| 20 | X68194 (SEQ ID 1) | D80012 (SEQ ID 2) | X69490 (SEQ ID 3) | D87343 (SEQ ID 7) | AB028985 (SEQ ID 13) | 0.87013 | 0.888889 | 0.879509 |
| 21 | X69490 (SEQ ID 3) | Z35491 (SEQ ID 5) | D87343 (SEQ ID 7) | AB028985 (SEQ ID 13) | AF070596 (SEQ ID 16):: | 0.811688 | 0.944444 | 0.878066 |
| 22 | X69490 (SEQ ID 3) | AL050050 (SEQ ID 4) | Z35491 (SEQ ID 5) | D87343 (SEQ ID 7) | M80244 (SEQ ID 10) | 0.811688 | 0.944444 | 0.878066 |
| 23 | X69490 (SEQ ID 3) | Z35491 (SEQ ID 5) | AB029003 (SEQ ID 6) | D87343 (SEQ ID 7) | M80244 (SEQ ID 10) | 0.810065 | 0.944444 | 0.877255 |
| 24 | X69490 (SEQ ID 3) | Z35491 (SEQ ID 5) | D87343 (SEQ ID 7) | D87343 (SEQ ID 7) | AL050025 (SEQ ID 18) | 0.806818 | 0.944444 | 0.875631 |
| 25 | X69490 (SEQ ID 3) | AL050050 (SEQ ID 4) | D87343 (SEQ ID 7) | M80244 (SEQ ID 10) | AB028985 (SEQ ID 13) | 0.806818 | 0.944444 | 0.875631 |
| 26 | X69490 (SEQ ID 3) | Z35491 (SEQ ID 5) | AB029003 (SEQ ID 6) | D87343 (SEQ ID 7) | AB018290 (SEQ ID 17) | 0.805195 | 0.944444 | 0.87482 |
| 27 | X69490 (SEQ ID 3) | Z35491 (SEQ ID 5) | D87343 (SEQ ID 7) | D13642 (SEQ ID 9) | AB018290 (SEQ ID 17) | 0.805195 | 0.944444 | 0.87482 |
| 28 | X68194 (SEQ ID 1) | D80012 (SEQ ID 2) | X69490 (SEQ ID 3) | D87343 (SEQ ID 7) | AB018290 (SEQ ID 17) | 0.86039 | 0.888889 | 0.874639 |
| 29 | X69490 (SEQ ID 3) | AL050050 (SEQ ID 4) | Z35491 (SEQ ID 5) | D87343 (SEQ ID 7) | M63175 (SEQ ID 11) | 0.801948 | 0.944444 | 0.873196 |

Figure 2D

| | | | | | | | |
|---|---|---|---|---|---|---|---|
| 30 | X68194 (SEQ ID 1) | D80012 (SEQ ID 2) | X69490 (SEQ ID 3) | AL050050 (SEQ ID 4) | D87343 (SEQ ID 7) | 0.857143 | 0.888889 | 0.873016 |
| 31 | D80012 (SEQ ID 2) | X69490 (SEQ ID 3) | D87343 (SEQ ID 7) | M80244 (SEQ ID 10) | AB018290 (SEQ ID 17) | 0.855519 | 0.888889 | 0.872204 |
| 32 | X69490 (SEQ ID 3) | AL050050 (SEQ ID 4) | Z35491 (SEQ ID 5) | AB029003 (SEQ ID 6) | D87343 (SEQ ID 7) | 0.797078 | 0.944444 | 0.870761 |
| 33 | X69490 (SEQ ID 3) | Z35491 (SEQ ID 5) | D87343 (SEQ ID 7) | M80244 (SEQ ID 10) | M63175 (SEQ ID 11) | 0.797078 | 0.944444 | 0.870761 |
| 34 | X68194 (SEQ ID 1) | X69490 (SEQ ID 3) | Z35491 (SEQ ID 5) | D87343 (SEQ ID 7) | D13642 (SEQ ID 9) | 0.797078 | 0.944444 | 0.870761 |
| 35 | X68194 (SEQ ID 1) | X69490 (SEQ ID 3) | Z35491 (SEQ ID 5) | D87343 (SEQ ID 7) | AB011170 (SEQ ID 20) | 0.857143 | 0.881944 | 0.869544 |
| 36 | X69490 (SEQ ID 3) | Z35491 (SEQ ID 5) | D87343 (SEQ ID 7) | M80244 (SEQ ID 10) | AF070596 (SEQ ID 16): | 0.793831 | 0.944444 | 0.869138 |
| 37 | X69490 (SEQ ID 3) | Z35491 (SEQ ID 5) | D87343 (SEQ ID 7) | M81118 (SEQ ID 15) | AF070596 (SEQ ID 16): | 0.793831 | 0.944444 | 0.869138 |
| 38 | X69490 (SEQ ID 3) | D87343 (SEQ ID 7) | D87343 (SEQ ID 7) | AB018290 (SEQ ID 17) | AL050025 (SEQ ID 18) | 0.792208 | 0.944444 | 0.868326 |
| 39 | X69490 (SEQ ID 3) | Z35491 (SEQ ID 5) | D87343 (SEQ ID 7) | D13642 (SEQ ID 9) | M80244 (SEQ ID 10) | 0.792208 | 0.944444 | 0.868326 |
| 40 | D80012 (SEQ ID 2) | X69490 (SEQ ID 3) | D87343 (SEQ ID 7) | M63175 (SEQ ID 11) | AF070596 (SEQ ID 16): | 0.847403 | 0.888889 | 0.868146 |

Figure 2E

| | | | | | | |
|---|---|---|---|---|---|---|
| 41 | X69490 (SEQ ID 3) | Z35491 (SEQ ID 5) | D87343 (SEQ ID 7) | AF070596 (SEQ ID 16): | AB011170 (SEQ ID 20) | 0.852273 | 0.881944 | 0.867109 |
| 42 | D80012 (SEQ ID 2) | X69490 (SEQ ID 3) | Z35491 (SEQ ID 5) | D87343 (SEQ ID 7) | AB011170 (SEQ ID 20) | 0.852273 | 0.881944 | 0.867109 |
| 43 | X69490 (SEQ ID 3) | Z35491 (SEQ ID 5) | AB029003 (SEQ ID 6) | D87343 (SEQ ID 7) | AB028985 (SEQ ID 13) | 0.787338 | 0.944444 | 0.865891 |
| 44 | X69490 (SEQ ID 3) | Z35491 (SEQ ID 5) | D87343 (SEQ ID 7) | D13642 (SEQ ID 9) | AB028985 (SEQ ID 13) | 0.787338 | 0.944444 | 0.865891 |
| 45 | X68194 (SEQ ID 1) | X69490 (SEQ ID 3) | D87343 (SEQ ID 7) | M80244 (SEQ ID 10) | AL050025 (SEQ ID 18) | 0.842532 | 0.888889 | 0.865711 |
| 46 | X69490 (SEQ ID 3) | AL050050 (SEQ ID 4) | D87343 (SEQ ID 7) | M80244 (SEQ ID 10) | AL050025 (SEQ ID 18) | 0.842532 | 0.888889 | 0.865711 |
| 47 | X69490 (SEQ ID 3) | AL050050 (SEQ ID 4) | Z35491 (SEQ ID 5) | D87343 (SEQ ID 7) | AJ009771 (SEQ ID 12) | 0.847403 | 0.881944 | 0.864674 |
| 48 | X69490 (SEQ ID 3) | Z35491 (SEQ ID 5) | D87343 (SEQ ID 7) | M63175 (SEQ ID 11) | AB011170 (SEQ ID 20) | 0.847403 | 0.881944 | 0.864674 |
| 49 | D80012 (SEQ ID 2) | X69490 (SEQ ID 3) | Z35491 (SEQ ID 5) | D87343 (SEQ ID 7) | M81118 (SEQ ID 15) | 0.784091 | 0.944444 | 0.864268 |
| 50 | X69490 (SEQ ID 3) | Z35491 (SEQ ID 5) | AB029003 (SEQ ID 6) | D87343 (SEQ ID 7) | D13642 (SEQ ID 9) | 0.782468 | 0.944444 | 0.863456 |

COMPOSITIONS FOR GLIOMA CLASSIFICATION

CROSS REFERENCE

This application claims priority to U.S. Provisional Patent Application Ser. No. 60/516,817 filed Nov. 3, 2003, which is incorporated by reference herein in its entirety.

INCORPORATION OF SEQUENCE LISTING

Two copies of the sequence listing (Sequence Listing Copy 1 and Sequence Listing Copy 2) on CD-ROMs, each containing the file named 03-968-US SeqListing.ST25, which is 7.35 MB and was created on Nov. 2, 2004, are herein incorporated by reference.

BACKGROUND

Primary central nervous system ("CNS") tumors, such as gliomas, are so named by the types of cells they contain, their location, or both. Detection of such tumors is difficult because of the diverse symptoms that patients with CNS tumors may present. Furthermore, once a CNS tumor is suspected, expensive imaging techniques are generally required for diagnosis, these various imaging techniques all suffer from one or more inadequacies, and none provide any definitive prognostic value. Laboratory tests such as electroencephalograms provide information on brain activity that might indicate a tumor, but are not able to identify and characterize CNS tumors or their prognosis.

Malignant gliomas are the most common primary brain tumor, and are classified histologically, with pathological diagnosis affecting prognostic estimation and therapeutic decision-making more than any other variable. (Nutt et al., Cancer Research 63:1602-1607 (2003)) Oligodendrogliomas, which are often chemosensitive, have a more favorable prognosis than glioblastomas, which are resistant to most available therapies. (Nutt, supra).

The maturation of microarray technology has enabled the routine collection of genome-wide gene expression (RNA) data. In cancer diagnostics, several authors have shown that microarray data collected from tumors may be useful in differential diagnosis, tumor staging, and prognosis. The data produced by these studies ideally represents a valuable resource for the development of new diagnostics. However, at present, the application of microarray technology requires steps in sample collection and sample preparation that inhibit routine clinical adoption.

In contrast, DNA-based markers are commonly used in cancer diagnostics. Diagnostic implementations utilizing fluorescence in situ hybridization (FISH) and RT-PCR technology are in widespread use. New diagnostic products based on such accepted technology will more quickly find clinical acceptance.

It is established that specific genetic aberrations are often associated with clinical characteristics. Examples include the association of 1 p/19 q deletions in breast cancer with improved response to chemotherapy, and the association of 8 q gain with poor prognosis in prostate cancer. Such aberrations have been detected with comparative genomic hybridization ("CGH"). However, the relationship between tumor karyotype and phenotype is often subtle, and may be difficult to determine from the typically available datasets consisting of low-resolution CGH data collected from a small number of samples.

Several studies have demonstrated the association of genetic aberrations with gene expression changes. In independent studies, Hyman et al (2002) and Pollack et al (2002) both found a strong relationship between high amplification and high expression in breast tumors. Crawley et al (2002) has reported on a data analysis method that accurately predicts regions of copy number aberrations in hepatocellular carcinomas using only gene expression data. These investigations support the notion that gene expression data can be used as a window to the underlying genetic defects, and thus the idea that a combined analysis of gene expression data and CGH copy number data with the aim of identifying DNA markers is viable.

SUMMARY OF THE INVENTION

The present invention provides novel compositions and their use in classifying gliomas. In a preferred embodiment, the methods are used to discriminate between oligodendrogliomas and glioblastomas.

BRIEF DESCRIPTION OF THE FIGURES

FIGS. 1A-D describe the various marker genes and related genomic sequences.

FIGS. 2A-E provide data on the most accurate 5 reporter set glioma biomarkers.

DETAILED DESCRIPTION OF THE INVENTION

All publications, GenBank Accession references, references to bacterial artificial chromosome ("BAC") accession numbers (sequences), patents and patent applications cited herein are hereby expressly incorporated by reference for all purposes.

Within this application, unless otherwise stated, the techniques utilized may be found in any of several well-known references such as: *Molecular Cloning: A Laboratory Manual* (Sambrook, et al., 1989, Cold Spring Harbor Laboratory Press), *Gene Expression Technology* (Methods in Enzymology, Vol. 185, edited by D. Goeddel, 1991. Academic Press, San Diego, Calif.), "Guide to Protein Purification" in *Methods in Enzymology* (M. P. Deutshcer, ed., (1990) Academic Press, Inc.); *PCR Protocols: A Guide to Methods and Applications* (Innis, et al. 1990. Academic Press, San Diego, Calif.), *Culture of Animal Cells: A Manual of Basic Technique*, $2^{nd}$ Ed. (R. I. Freshney. 1987. Liss, Inc. New York, N.Y.), *Gene Transfer and Expression Protocols*, pp. 109-128, ed. E. J. Murray, The Humana Press Inc., Clifton, N.J.), and the Ambion 1998 Catalog (Ambion, Austin, Tex.).

The present invention provides novel compositions and methods for their use in classifying gliomas, particularly to distinguish between glioma types such as oligodendrogliomas and glioblastomas. Malignant gliomas are the most common primary brain tumor, and are classified histologically, with pathological diagnosis affecting prognostic estimation and therapeutic decision-making more than any other variable. (Nutt et al., Cancer Research 63:1602-1607 (2003)) Oligodendrogliomas, which are often chemosensitive, have a more favorable prognosis than glioblastomas, which are resistant to most available therapies. (Nutt, supra). Thus, the ability to more accurately classify gliomas into oligodendrogliomas and glioblastomas will provide information on glioma diagnosis, patient prognosis in the presence or absence of chemotherapy, a predicted optimal course for treatment of the patient, and patient life expectancy.

The inventors of the present invention have identified compositions to permit improved glioma classification over that possible using prior art diagnostic and predictive compositions and methods. Prior art methods for genetic-based prognosis have either focused on (a) analysis of expression or copy number of single gene or genomic region, which is likely to be relevant for only a small subset of tumors; or on (b) analysis of a large array of many genes or genomic regions, which are impractical for use in clinical diagnostic laboratories and most research facilities.

These compositions are defined relative to the following nucleic acid sequences that are identified herein as being useful as markers for glioma classification:

Gen Bank Accession No. X68194:*H.sapiens* h-Sp1 mRNA (SEQ ID NO:1)
Gen Bank Accession No.D80012:Human mRNA for KIAA0190 gene (SEQ ID NO:2)
Gen Bank Accession No. X69490:*H.sapiens* MRNA for titin (SEQ ID NO:3)
Gen Bank Accession No. AL050050:*Homo sapiens* mRNA; cDNA DKFZp566D133 (from clone DKFZp566D133) (SEQ ID NO:4)
Gen Bank Accession No. Z35491 :*H.sapiens* mRNA for novel glucocorticoid receptor-associated protein (SEQ ID NO:5)
Gen Bank Accession No. AB029003:*Homo sapiens* mRNA for KIAA1080 protein (SEQ ID NO:6)
Gen Bank Accession No. D87343:*Homo sapiens* mRNA for DCRA (SEQ ID NO:7)
Gen Bank Accession No. X17644:Human GST1-Hs mRNA for GTP-binding protein (SEQ ID NO:8)
Gen Bank Accession No. D13642:Human mRNA for KIAA0017 gene (SEQ ID NO:9)
Gen Bank Accession No. M80244:Human E16 Mrna (SEQ ID NO:10)
Gen Bank Accession No. M63175:Human autocrine motility factor receptor MRNA (SEQ ID NO:11)
Gen Bank Accession No. AJ009771:*Homo sapiens* MRNA for putative RING finger protein (SEQ ID NO:12)
Gen Bank Accession No. AB028985:*Homo sapiens* MRNA for KIAA1062 protein (SEQ ID NO:13)
Gen Bank Accession No. M81118:Human alcohol dehydrogenase chi polypeptide (ADH5) gene (SEQ ID NO:15)
Gen Bank Accession No. AF070596:*Homo sapiens* clone 24796 mRNA sequence (SEQ ID NO:16)
Gen Bank Accession No. AB018290:*Homo sapiens* mRNA for KIAA0747 protein (SEQ ID NO:17)
Gen Bank Accession No. AL050025:*Homo sapiens* mRNA; cDNA DKFZp564D066 (from clone DKFZp564D066) (SEQ ID NO:18)
Gen Bank Accession No. AC002394:Human Chromosome 16 BAC clone CIT987SK-A-211C6 (SEQ ID NO:19)
Gen Bank Accession No. AB011170:*Homo sapiens* mRNA for KIAA0598 protein (SEQ ID NO:20)

While statistically significant, we believe that the clinical diagnostic utility of subsets of these nineteen gene markers will be greater than the clinical diagnostic utility of individual genes. Such combinations consisting of more than two different probe sets may better classify the complexity of genomic aberrations associated with particular phenotypes in gliomas.

Many studies have demonstrated that when genomic regions are amplified (as in a tumor), the amplified region most commonly consists of a number of genes, in spite of the tendency to describe such amplified genomic regions in terms of a single gene. (Barlund et al., cancer Res. 2000 Oct. 1; 60(19):5340-4; Kauraniemi et al., Cancer Res. 2001 Nov 15; 61(22):8235-40; Pollack et al., 2002; Hyman et al., Cancer Res. 2002 Nov. 1; 62(21):6240-5; Monni et al., Proc. Natl. Acad. Sci. USA 2001 May 8; 98(10):5711-6). For example, a "her-2" amplified genomic region generally contains the her-2 gene and many flanking genes in the region of altered copy number. Physical distances between the genes used in these studies, as described in publicly available databases (for example, UCSC human genome web site at genome.ucsc.edu) reveals that, while the sizes of the altered copy number region vary among tumors, the size of an "average" altered copy number region is reasonably estimated as at least 1 megabase.

Thus, in a first aspect, the present invention provides compositions comprising a glioma biomarker, wherein the glioma biomarker consists of between 2 and 47 different probe sets, wherein at least 40% of the different probe sets comprise or consist of one or more isolated polynucleotides that selectively hybridize to a genomic region selected from the group consisting of 2q31.2; 4q23; 7q22.3; 9q31.2; 9p21-p13; 9q34.3; 10q26.13; 12q13.2; 14q13.2; 15q24.1; 15q22.2; 16q13.13; 16q22.1; 16q22.2; 16q24.1; 16q24.2; 16p12.2; 16p12.3; and 21q22.13; wherein the different probe sets in total selectively hybridize to at least two of the recited genomic regions.

The term "glioma biomarker" as used herein for all of the aspects and embodiments of the invention, refers to its use in classifying gliomas. The recited genomic regions correspond to the genomic position of the markers identified by the inventors of the present invention, which permit improved glioma classification over that possible using prior art diagnostic and predictive compositions and methods. FIG. 1 provides a detailed summary of the genes, their GenBank accession number, genomic region at which the genes are located, and the names and SEQ ID NOS. of bacterial artificial chromosomes ("BAC") that contain the gene (discussed in more detail below).

Thus, the compositions of the present invention are useful, for example, in classifying human gliomas. The compositions can be used, for example, to identify one or more genomic regions as present in an abnormal copy number (for example, more than two copies of the gene per cell in a chromosome spread or fewer than two copies) in a nucleic acid sample from a human specimen, such as brain tissue samples (including but not limited to biopsies and solid tumor samples), cerebrospinal fluid, blood samples, (such as blood smears), and bone marrow cells, with special attention given to circulating tumor cells that have been shed from a tumor.

Alternatively, certain embodiments of the compositions (as discussed in more detail below) can be used to classify gliomas by determining the expression levels in tissue of the mRNA encoded by the genes recited above.

The compositions according to each of the aspects and embodiments of the invention provide an improvement over prior art glioma classification compositions, which require many hundreds or thousands of probes to classify a glioma, and do so with reduced accuracy compared to the glioma biomarker of the present invention. As a result, the compositions of the present invention are much more amenable to use in clinical diagnostic testing than are prior art methods for glioma characterization.

The term "polynucleotide" as used herein with respect to each aspect and embodiment of the invention refers to DNA or RNA, preferably DNA, in either single- or double-stranded form. It includes the recited sequences as well as their complementary sequences, which will be clearly understood by those of skill in the art. The term "polynucleotide" encompasses nucleic acids containing known analogues of natural nucleotides which have similar or improved binding properties, for the purposes desired, as the reference polynucleotide. The term also encompasses nucleic-acid-like structures with synthetic backbones. DNA backbone analogues provided by the invention include phosphodiester, phosphorothioate, phosphorodithioate, methylphosphonate, phosphoramidate, alkyl phosphotriester, sulfamate, 3'-thioacetal, methylene(methylimino), 3'-N-carbamate, morpholino carbamate, and peptide nucleic acids (PNAs), methylphosphonate linkages or alternating methylphosphonate and phosphodiester linkages (Strauss-Soukup (1997) Biochemistry 36:8692-8698), and benzylphosphonate linkages, as discussed in U.S. Pat.

No. 6,664,057; see also Oligonucleotides and Analogues, a Practical Approach, edited by F. Eckstein, IRL Press at Oxford University Press (1991); Antisense Strategies, Annals of the New York Academy of Sciences, Volume 600, Eds. Baserga and Denhardt (NYAS 1992); Milligan (1993) J. Med. Chem. 36:1923-1937; Antisense Research and Applications (1993, CRC Press).

In each of the aspects and embodiments of the compositions and methods of the present invention, it is further preferred that the isolated polynucleotides are labeled with a detectable label. In a preferred embodiment, the detectable labels on the isolated polynucleotides in one probe set are all the same, and are distinguishable from the detectable labels on the isolated polynucleotides in the other probe sets in a given glioma biomarker. Such labeling of the isolated polynucleotides facilitates differential determination of the signals from different reporter sets in a given glioma biomarker. Useful detectable labels include but are not limited to radioactive labels such as $^{32}P$, $^{3}H$, and $^{14}C$; fluorescent dyes such as fluorescein isothiocyanate (FITC), rhodamine, lanthanide phosphors, Texas red, and ALEXIS™ (Abbott Labs), CY™ dyes (Amersham); electron-dense reagents such as gold; enzymes such as horseradish peroxidase, beta-galactosidase, luciferase, and alkaline phosphatase; colorimetric labels such as colloidal gold; magnetic labels such as those sold under the mark DYNABEADS™; biotin; dioxigenin; or haptens and proteins for which antisera or monoclonal antibodies are available. The label can be directly incorporated into the polynucleotide, or it can be attached to a molecule which hybridizes or binds to the polynucleotide. The labels may be coupled to the isolated polynucleotides by any means known to those of skill in the art. In a various embodiments, the isolated polynucleotides are labeled using nick translation, PCR, or random primer extension (see, e.g., Sambrook et al. supra). Methods for detecting the label include, but are not limited to spectroscopic, photochemical, biochemical, immunochemical, physical or chemical techniques.

An "isolated" polynucleotide as used herein for all of the aspects and embodiments of the invention is one which is separated from other nucleic acid molecules which are present in the natural source of the polynucleotide. Preferably, an "isolated" polynucleotide is free of sequences which naturally flank the polynucleotide in the genomic DNA of the organism from which the nucleic acid is derived, except as specifically described herein. Moreover, an "isolated" polynucleotide is substantially free of other cellular material, gel materials, and culture medium when produced by recombinant techniques, or substantially free of chemical precursors or other chemicals when chemically synthesized. The polynucleotides of the invention may be isolated from a variety of sources, such as by PCR amplification from genomic DNA, mRNA, or cDNA libraries derived from mRNA, using standard techniques; or they may be synthesized in vitro, by methods well known to those of skill in the art, as discussed in U.S. Pat. No. 6,664,057 and references disclosed therein. Synthetic polynucleotides can be prepared by a variety of solution or solid phase methods. Detailed descriptions of the procedures for solid phase synthesis of polynucleotide by phosphite-triester, phosphotriester, and H-phosphonate chemistries are widely available. (See, for example, U.S. Pat. No. 6,664,057 and references disclosed therein). Methods to purify polynucleotides include native acrylamide gel electrophoresis, and anion-exchange HPLC, as described in Pearson (1983) J. Chrom. 255:137-149. The sequence of the synthetic polynucleotides can be verified using standard methods.

As used herein with respect to all aspects and embodiments of the invention, a "probe set" refers to a group of one or more polynucleotides that each selectively hybridize to the same target (for example, a specific genomic region or mRNA) that correlates with glioma characterization, including glioma diagnosis, prognosis, and classification. Thus, a single "probe set" may comprise any number of different isolated polynucleotides that selectively hybridize to for a given target. For example, a probe set that selectively hybridizes to SEQ ID NO:10 may comprise probes for a single 100 nucleotide segment of SEQ ID NO:10, or for a 100 nucleotide segment of SEQ ID NO:10 and also a different 100 nucleotide segment of SEQ ID NO:10, or both these in addition to a separate 10 nucleotide segment of SEQ ID NO:10, or 500 different 10 nucleotide segments of SEQ ID NO:10 (such as, for example, fragmenting a larger probe into may individual short polynucleotides). Those of skill in the art will understand that many such permutations are possible.

In this first aspect, the glioma biomarker can be any glioma biomarker that contains between 2 and 47 probe sets as defined herein, wherein at least 40% of the probe sets comprise or consist of one or more isolated polynucleotides that selectively hybridize to one of the recited genomic regions. Such glioma biomarkers thus can contain other probe sets for use in glioma classification, diagnosis, or analysis, so long as at least 40% of the probe sets comprise one or more isolated polynucleotides that selectively hybridize to one of the recited genomic regions, and so long as no more than 47 probe sets are present in the glioma biomarker.

In preferred embodiments of the first aspect of the invention, at least 45%, 50%, 55%, 60%, 65%, 70%, 80%, 85%, 90%, 95%, or 100% of the probe sets comprise or consist of one or more isolated polynucleotides that selectively hybridize to one of the recited genomic regions. As will be apparent to those of skill in the art, as the percentage of probe sets that comprise or consist of one or more isolated polynucleotides that selectively hybridize to one of the recited genomic regions increases, the maximum number of probe sets in the glioma biomarker will decrease accordingly. Thus, for example, where at least 80% of the probe sets comprise or consist of one or more isolated polynucleotides that selectively hybridize to one of the recited genomic regions, the glioma marker will consist of between 2 and 23 probe sets. Those of skill in the art will recognize the various other permutations encompassed by the compositions according to the various aspects of the invention.

The composition of each aspect and embodiment of the invention may further comprise other polynucleotide components that are beneficial for use in combination with the glioma biomarker, such as competitor nucleic acids and other control sequences (such as sequences to provide a standard of hybridization for comparison, etc.) Such other polynucleotide components are not probe sets for purposes of the compositions and methods of the invention. The compositions may optionally comprise other components, including but not limited to buffer solutions, hybridization solutions, and reagents for storing the nucleic acid compositions.

As used herein with respect to each aspect and embodiment of the invention, the term "selectively hybridizes" means that the isolated polynucleotides bind to the particular genomic region or other target to form a hybridization complex, and minimally or not at all to other sequences. The exact conditions used will depend on the length of the polynucleotide probes employed, their GC content, as well as various other factors as is well known to those of skill in the art. (See, for example, Tijssen (1993) Laboratory Techniques in Biochemistry and Molecular Biology—Hybridization with Nucleic Acid Probes part I, chapt 2, "Overview of principles of hybridization and the strategy of nucleic acid probe assays," Elsevier, N.Y. ("Tijssen")). In one embodiment, stringent hybridization and wash conditions are selected to be about 5° C. lower than the thermal melting point (Tm) for the specific sequence at a defined ionic strength and pH. The Tm is the temperature (under defined ionic strength and pH) at which 50% of the target sequence hybridizes to a perfectly matched probe. High stringency conditions are selected to be equal to the Tm for a particular probe. An example of stringent conditions are those that permit selective hybridization of the isolated polynucleotides to the genomic or other target nucleic acid to form hybridization complexes in 0.2×SSC at 65° C. for a desired period of time, and wash conditions of 0.2×SSC at 65° C. for 15 minutes. It is understood that these conditions may be duplicated using a variety of buffers and temperatures. SSC (see, e.g., Sambrook, Fritsch, and Maniatis, in: Molecular Cloning, A Laboratory Manual, Cold Spring Harbor Laboratory Press, 1989) are well known to those of skill in the art, as are other suitable hybridization buffers.

In various preferred embodiments of this first aspect of the invention, the glioma biomarker includes three, four, five, six, seven, eight, nine, ten, eleven, twelve, thirteen, fourteen, fifteen, sixteen, seventeen, eighteen, or nineteen different probe sets that comprise one or more isolated polynucleotides that selectively hybridize to a genomic region selected from the group consisting of 2q31.2; 4q23; 7q22.3; 9q31.2; 9p21-p13; 9q34.3; 10q26.13; 12q13.2; 14q13.2; 15q24.1; 15q22.2; 16q13.13; 16q22.1; 16q22.2; 16q24.1; 16q24.2; 16p12.2; 16p12.3; and 21q22.13, wherein the different probe sets in total selectively hybridize to at least three, four, five, six, seven, eight, nine, ten, eleven, twelve, thirteen, fourteen, fifteen, sixteen, seventeen, eighteen, or nineteen of the recited genomic regions. In each of these embodiments, it is further preferred that at least 45%, 50%, 55%, 60%, 65%, 70%, 80%, 85%, 90%, 95%, or 100% of the probe sets for a given glioma biomarker comprise or consist of one or more isolated polynucleotides that selectively hybridize to one of the recited genomic regions.

Those of skill in the art are aware that multiple resources are available to identify specific nucleotide sequences associated with these genomic regions. In one example, such sequences can be found as follows:

Go to the UCSC web site at, genome.ucsc.edu/index.html?org=Human. At this site, select the Genome Browser on the menu at the left. Then in the "position" field enter, (in this format, e.g. for chromosome 16p13): 16:11,000,000-12,000,000 and then select "jump" (position entries have to be either by gene name, clone name, accession number, etc. or base pair position, usually in millions) Once the image of the chromosome is in view, which has the base pairs at the top of the image, and the chromosome bands immediately below, the navigation tools can be used to zoom in or out, move to the left or right as necessary. To get to the sequence itself (for 16p13 as an example), select the band designation within the image, which leads to the "Chromosome Bands Localized by FISH Mapping Clones (p13.2)" page, which has the "View DNA for this feature" button. Choose the "View DNA . . ." button which leads to the "Get DNA in Window". At the bottom of that page choose the "Get DNA" button, and the sequence appears. At the very top of the sequence page the exact base pairs are shown.

Those of skill in the art will understand how to apply this disclosure to identify nucleotide sequences with other genomic regions of interest.

In a second aspect, the invention provides compositions comprising a glioma biomarker consisting of between 2 and 47 different probe sets, wherein at least 40% of the different probe sets comprise one or more isolated polynucleotide sequences that selectively hybridize to a nucleic acid sequence according to formula 1, or its complement:

X1-X2-X3 wherein X2 is a human genomic nucleic acid sequence selected from the group consisting of SEQ ID NO: 19, SEQ ID NO:21 to SEQ ID NO:47, and SEQ ID NO:49-57 (see FIG. 1); and wherein X1 and X3 are independently 0-500 kB of human genomic nucleic acid sequences flanking X2 in the human genome; and wherein the different polynucleotide probe sets in total selectively hybridize to at least two non-overlapping genomic sequences according to formula 1.

SEQ ID NO: 19, SEQ ID NO:21 to SEQ ID NO:47, and SEQ ID NO:49-57 provide the human genomic sequence encompassing the marker genes (and portions of the genomic regions of the first aspect of the invention) discussed above, cloned into BAC vectors. (See FIG. 1) As will be apparent to those of skill in the art in reviewing FIG. 1, genomic regions for each of the cloned markers for glioma classification described above (SEQ ID NO:1-13 and 15-20) are disclosed as SEQ ID NO: 19, SEQ ID NO:21 to SEQ ID NO:47, and SEQ ID NO:49-57. For some of the 19 cloned markers, multiple overlapping BAC insert sequences are provided (see, for Example, SEQ ID NOS:23-25, which are overlapping genomic fragments that each include at least a portion of the gene for KIAA0190 (SEQ ID NO:2).

In various preferred embodiments of this second aspect of the invention, the glioma biomarker consists of three, four, five, six, seven, eight, nine, ten, eleven, twelve, thirteen, fourteen, fifteen, sixteen, seventeen, eighteen, or nineteen different probe sets that selectively hybridize to a nucleic acid sequence according to formula 1, or its complement. In each of these embodiments, it is further preferred that at least 45%, 50%, 55%, 60%, 65%, 70%, 80%, 85%, 90%, 95%, or 100% of the probe sets for a given glioma biomarker comprise or consist of one or more isolated polynucleotides that selectively hybridize to a nucleic acid sequence according to formula 1, or its complement, wherein the different polynucleotide probe sets in total selectively hybridize to at least three, four, five, six, seven, eight, nine, ten, eleven, twelve, thirteen, fourteen, fifteen, sixteen, seventeen, eighteen, or nineteen non-overlapping genomic sequences according to formula 1.

As will be apparent to those of skill in the art, as the percentage of probe sets that comprise or consist of one or more isolated polynucleotides that selectively hybridize to a nucleic acid sequence according to formula 1, or its complement, the maximum number of probe sets in the glioma biomarker will decrease accordingly. Thus, for example, where at least 80% of the probe sets comprise or consist of one or more isolated polynucleotides that selectively hybridize to a nucleic acid sequence according to formula 1, or its complement, the glioma marker will consist of between 2 and 23 probe sets. Those of skill in the art will recognize the various other permutations encompassed by the compositions according to the various embodiments of the second aspect of the invention.

In a further preferred embodiment of each of the above embodiments of the second aspect of the invention, X1 and X3 are 0.

In a preferred embodiment of the various embodiments of the second aspect of the invention, the different probe sets of a glioma biomarker comprise or consist of one or more polynucleotide sequences of at least 10 nucleotides of a nucleic acid sequence according to formula 1, or its complement. In a further preferred embodiment, of each of the above embodiments, X1 and X3 are 0.

In various further preferred embodiments of each of the above embodiments of the first and second aspects of the invention, the polynucleotides in the probe set independently comprise or consist of at least 10, 15, 20, 25, 30, 35, 40, 45, 50, 55, 60, 65, 70, 75, 80, 85, 90, 95, 100, 150, 200, 250, 300, 350, 400, 450, 500, 550, 600, 650, 700, 750, 800, 850, 900, 950, 1000, 1100, 1200, 1300, 1400, 1500, 1600, 1700, 1800, 1900, 2000, 2100, 2200, 2300, 2400, 2500, 2600, 2700, 2800, 2900, 3000, 3100, 3200, 3300, 3400, 3500, 3600, 3700, 3800, 3900, 4000, 4100, 4200, 4300, 4400, 4500, 4600, 4700, 4800, 4900, 5000, 5100, 5200, 5300, 5400, 5500, 5600, 5700, 5800, 5900, 6000, 6100, 6200, 6300, 6400, 6500, 6600, 6700, 6800, 6900, 7000, 7100, 7200, 7300, 7400, 7500, 7600, 7700, 7800, 7900, 8000, 8100, 8200, 8300, 8400, 8500, 8600, 8700, 8800, 8900, 9000, 9100, 9200, 9300, 9400, 9500, 9600, 9700, 9800, 9900, 10,000; 15,000; 20,000; 25,000; 30,000; 35,000; 40,0000; 45,000; 50,000; 60,000; 70,000; 80,000; 90,000; 100,000; 110,000; 120,000; 130,000; 140,000; 150,000; 160,000; 170, 000; 180,000; 190,000; 200,000; 210,000; or 220,000 nucleotides of the relevant sequence.

The BACS disclosed herein are as defined on the University of California at Santa Cruz (UCSC) Genome Browser on the Human April 2003 Freeze and are available from the Children's Hospital Oakland Research Institute (CHORI) at www.bacpac.chori.org. The human genomic inserts cloned into the BACS disclosed herein range in size from approximately 100 kB to 220 kB in length. The applicants have also provided a sequence listing that contains the sequence of the human genomic insert cloned into the BACs disclosed herein.

The BACs in this application are included in the "32K BAC re-array" at CHORI. To get to the 32K re-array, the CHORI BACPAC Resources Center (BPRC) can be accessed at the web site bacpac.chori.org/. Choose "Libraries" from the "Quick Links" menu on CHORI web page to get to the "Library Resources" page. On the "Library Resources" page, select "-By library type" and then select: "BAC Rearray CHORI-Human 32K Set: Chromosome Specific Rearray set." This takes you to the "Human genome high-resolution BAC re-arrayed clone set (the "32k set")" page. On that page, under: "Related Links:" select "bcgsc.ca/lab/mapping/bacrearray/human/," which takes you to: Canada's Michael Smith Genome Sciences Center "Full-Genome BAC Rearrays" page. At the very bottom of that page is a browser link to the UCSC Genome page. Select the word "browse" in the "Browser" paragraph, which returns to the UCS site. Enter the accession number in the "position" field (e.g. enter "X68194"), select "jump" and the BACs that contain that accession number will automatically show up. Select the BAC clone of interest. For example, selecting "RP11-193P05" leads to the Custom Track" for that BAC. On the Custom Track page are the position numbers for that BAC (e.g. Position: "chr7:105166071-105313293", (and other information) and a link to view The DNA: "View DNA for this feature". Choose the "View DNA" link to get to the "Get DNA for" page, and then choose the "get DNA" button on the bottom of that page. The complete sequence for that BAC is retrieved. One exception: UCSC doesn't find accession number M81118; this can be found by searching "ADH5", and choosing the "chi" subunit.

Furthermore, human genomic nucleic acid sequences flanking the genomic sequence cloned in the BAC of interest can also be retrieved as follows:

Once the BAC of interest has been found in the database, as described above, the sequence of each BAC be found by selecting the name of the BAC. The first click connects to a "Custom Track" for that BAC. On the Custom Track page there is an option called "View DNA for this feature", which is a link to the "Get DNA" window, for that specific BAC. Once the "Get DNA" page for a specific BAC has been called up, the "Get DNA" button retrieves the complete DNA sequence for that BAC clone. Furthermore, sequences flanking the BAC of interest can also be retrieved from the "Get DNA" page by using "Sequence Retrieval Option": the number of bases desired both upstream and downstream of the BAC are entered and, and those flanking sequences are then retrieved along with the sequence of the BAC itself. Furthermore, the detailed information on the BACS provided herein discloses the genomic location in terms of base pair position of the human genomic insert cloned in BACS as of the Human April 2003 Freeze.

As will be understood by those of skill in the art, the human genome sequence is frequently updated, with the updates made available to the public. Those of skill in the art will thus be able to identify the human genomic nucleic acid sequences flanking the genomic sequence cloned in the BAC of interest and disclosed herein by accessing the human genome information at (e.g. http://genome.ucsc.edu/). Therefore, the "flanking sequences" as recited herein refer to flanking sequences as disclosed on the web sites provided above, as well as updates thereto. For example, one can go to the CHORI site as disclosed above and review the BAC information as of the Human April 2003 Freeze to get the relative base pair position on the chromosome that the human genomic insert cloned in a BAC of interest was derived from. By reviewing the human genome sequence data available as of the Human April 2003 Freeze (as described above), one of skill in the art can obtain the nucleic acid sequences flanking the human genomic insert cloned in a BAC of interest disclosed herein. Those of skill in the art can further use this sequence to identify human genomic nucleic acid sequences flanking the human genomic insert cloned in a BAC of interest from this same site as currently updated in the human genome sequence.

In a third aspect, the present invention provides compositions comprising a glioma biomarker consisting of between 2 and 47 different probe sets, wherein at least 40% of the different probe sets comprise one or more isolated polynucleotides that selectively hybridize to a nucleic acid sequence according to one of SEQ ID NO:1-13 and 15-20 or their complements; wherein the different probe sets in total selectively hybridize to at least two of the recited nucleic acid sequences according to SEQ ID NO:1-13 and 15-20 or their complements.

In various preferred embodiments of the third aspect of the invention, the composition comprises a glioma biomarker consisting of three, four, five, six, seven, eight, nine, ten, eleven, twelve, thirteen, fourteen, fifteen, sixteen, seventeen, eighteen, or nineteen different probe sets that selectively hybridize to a nucleic acid sequence according to one of SEQ ID NO:1-13 and 15-20 or their complements, wherein the different probe sets in total selectively hybridize to at least three, four, five, six, seven, eight, nine, ten, eleven, twelve, thirteen, fourteen, fifteen, sixteen, seventeen, eighteen, or nineteen of the recited nucleic acid sequences according to SEQ ID NO:1-13 and 15-20 or their complements. In each of these embodiments, it is further preferred that at least 45%, 50%, 55%, 60%, 65%, 70%, 80%, 85%, 90%, 95%, or 100% of the probe sets for a given glioma biomarker comprise or consist of one or more isolated polynucleotides that selectively hybridize to a nucleic acid sequence according to SEQ ID NO:1-13 and 15-20, or their complements. As will be apparent to those of skill in the art, as the percentage of probe sets that comprise or consist of one or more isolated polynucleotides that selectively hybridize to a nucleic acid sequence according to SEQ ID NO:1-13 and 15-20, or their complements, the maximum number of probe sets in the glioma biomarker will decrease accordingly. Thus, for example, where at least 80% of the probe sets comprise or consist of one or more isolated polynucleotides that selectively hybridize to a nucleic acid sequence according to SEQ ID NO:1-13 and 15-20, or their complements, the glioma marker will consist of between 2 and 23 probe sets. Those of skill in the art will recognize the various other permutations encompassed by the compositions according to the various embodiments of the third aspect of the invention.

In a preferred embodiment of the various embodiments of the third aspect of the invention, the different probe sets of a glioma biomarker comprise or consist of one or more polynucleotide sequences of at least 10 nucleotides of a nucleic acid sequence according to SEQ ID NO:1-13 and 15-20, or their complements.

The nucleic acid compositions of this third aspect of the invention are especially preferred for analysis of RNA expression from the genes in a tissue of interest, such as brain tissue samples (including but not limited to biopsies and solid tumor samples), cerebrospinal fluid, blood samples, (such as blood smears), and bone marrow cells, with special attention given to circulating tumor cells that have been shed from a tumor. Such polynucleotides according to this aspect of the invention can be of any length that permits selective hybridization to the nucleic acid of interest. In various preferred embodiments, the isolated polynucleotides according to this aspect comprise or consist of at least 10, 15, 20, 25, 30, 35, 40, 45, 50, 55, 60, 65, 70, 75, 80, 85, 90, 95, 100, 150, 200, 250, 300, 350, 400, 450, 500, 550, 600, 650, 700, 750, 800, 850, 900, 950, or 1000 nucleotides according to a nucleic acid sequence selected from the group consisting of SEQ ID NO:1-13 and 15-20, or their complements. In a further embodiment of this aspect of the invention, an isolated polynucleotide according to this third aspect of the invention comprise or consist of a nucleic acid sequence according to one of SEQ ID NO:1-13 and 15-20, or their complements.

FIG. 2 provides a ranking of the overall accuracy in classifying gliomas of preferred combinations of 5 gene marker sets. Thus, in a further embodiment of each of the above aspects and embodiments, the glioma biomarkers include reporter sets to selectively hybridize to each of the genes, their corresponding BAC sequences, or the corresponding genomic regions (compare FIGS. 1 and 2) present in one of marker sets 1 to 50 shown in FIG. 2.

The compositions of the various aspects and embodiments of the invention can be in lyophilized form, or preferably comprise a solution containing the isolated polynucleotides, including but not limited to buffer solutions, hybridization solutions, and solutions for keeping the compositions in storage. Such a solution can be made as such, or the composition can be prepared at the time of hybridizing the polynucleotides to a target sequence, as discussed below.

Alternatively, the compositions can be placed on a solid support, such as in a microarray, bead, or microplate format. The term "microarray" as used herein is a plurality of probe sets immobilized on a solid surface to which sample nucleic acids are hybridized (such as glioma MRNA or derived cDNA).

Thus, in a fourth aspect, the present invention provides microarrays comprising a support structure on which are arrayed probe sets according to the compositions of the invention, as disclosed above. In this aspect, a single probe set can be present at a single location on the array, or different polynucleotides from a single probe set can be present at different and defined locations on the array.

In this aspect, the polynucleotides are immobilized on a microarray solid surface. Other nucleic acid sequences, such as reference or control nucleic acids, can be optionally immobilized on the solid surface as well. Methods for immobilizing nucleic acids on a variety of solid surfaces are well known to those of skill in the art. A wide variety of materials can be used for the solid surface. Examples of such solid surface materials include, but are not limited to, nitrocellulose, nylon, glass, quartz, diazotized membranes (paper or nylon), silicones, polyformaldehyde, cellulose, cellulose acetate, paper, ceramics, metals, metalloids, semiconductor materials, coated beads, magnetic particles; plastics such as polyethylene, polypropylene, and polystyrene; and gel-forming materials, such as proteins (e.g., gelatins), lipopolysaccharides, silicates, agarose and polyacrylamides.

A variety of different materials may be used to prepare the microarray solid surface to obtain various properties. For example, proteins (e.g., bovine serum albumin) or mixtures of macromolecules (e.g., Denhardt's solution) can be used to minimize non-specific binding, simplify covalent conjugation, and/or enhance signal detection. If covalent bonding between a compound and the surface is desired, the surface will usually be functionalized or capable of being functionalized. Functional groups which may be present on the surface and used for linking include, but are not limited to, carboxylic acids, aldehydes, amino groups, cyano groups, ethylenic groups, hydroxyl groups, and mercapto groups. Methods for linking a wide variety of compounds to various solid surfaces are well known to those of skill in the art.

In a preferred embodiment of this fourth aspect, the locations on the array containing probe sets of the present invention range in size between 1 µm and 1 cm in diameter, more preferably between 1 µm and 5 mm in diameter, and even more preferably between 5 µm and 1 mm in diameter. The polynucleotides of the probe sets may be arranged on the solid surface at different densities, depending on factors such as the nature of the label, the solid support, and the size of the polynucleotide. One of skill will recognize that each location on the microarray may comprise a mixture of polynucleotides of different lengths and sequences from a given probe set. The length and complexity of the polynucleotides fixed onto the locations can be adjusted to provide optimum hybridization and signal production for a given hybridization procedure, and to provide the required resolution.

In a fifth aspect, the present invention provides methods for classifying a glioma, comprising (a) contacting a nucleic acid sample obtained from a subject having a glioma with nucleic acid probes that, in total, selectively hybridize to two or more genomic regions selected from the group consisting of 2q31.2; 4q23; 7q22.3; 9q31.2; 9p21-p13; 9q34.3; 10q26.13; 12q13.2; 14q13.2; 15q24.1; 15q22.2; 16q13.13; 16q22.1; 16q22.2; 16q24.1; 16q24.2; 16p12.2; 16p12.3; and 21q22.13; wherein the contacting occurs under conditions to promote selective hybridization of the one or more nucleic acid probes to the two or more genomic regions;

(b) detecting formation of hybridization complexes;

(c) determining whether one or more of the genomic regions are present in an altered copy number in the nucleic acid sample; and (d) correlating a decreased copy number of one or more of the genomic regions with a classification of the glioma as an oligodendroglioma, and correlating an absence of decreased copy number for one or more of the genomic regions with a classification of the glioma as a glioblastoma.

Further optional steps can include, but are not limited to, pre-hybridization of the nucleic acid sample and use of competitor nucleic acids.

The nucleic acid sample used in the methods of the present invention can be from any source useful in characterizing a glioma, including but not limited to brain tissue samples (including but not limited to biopsies and solid tumor samples), cerebrospinal fluid, blood samples, (such as blood smears), and bone marrow cells, with special attention given to circulating tumor cells that have been shed from a tumor. The nucleic acid sample is preferably a cellular DNA or RNA sample, such as a sample prepared for in situ hybridization.

In the fifth aspect of the invention, a decreased copy number of one or more of the genomic regions correlates with a classification of the glioma as an oligodendroglioma, and an absence of decreased copy number for one or more of the genomic regions correlates with a classification of the glioma as a glioblastoma Thus, the methods of this aspect of the invention provide the ability to more accurately classify gliomas into oligodendrogliomas and glioblastomas, and provide information on glioma diagnosis, patient prognosis in the presence or absence of chemotherapy, a predicted optimal course for treatment of the patient, and patient life expectancy. For example, classification of the glioma as an oligodendroglioma indicates that the patient is more likely to respond to chemotherapy treatment then if the glioma was classified as a glioblastoma.

Thus, the invention further provides methods for treating a glioma patient, comprising carrying out the methods for classifying a glioma according to the different aspects and embodiments of the present invention, and then determining a course of treatment based on the results of the classification.

In various preferred embodiments of the methods of the fifth aspect of the invention, the nucleic acid probes are selected from the various aspects and embodiments of the compositions disclosed above. In a most preferred embodiment, the polynucleotides of the probe sets comprise a detectable label, as disclosed above, and in particular the different probe sets comprise distinguishable detectable labels, to facilitate analysis of which genomic region(s) is/are the site of the an altered copy number.

In various other preferred embodiments of the methods of the invention, the one or more nucleic acid probes, in total, selectively hybridize to three, four, five, six, seven, eight, nine, ten, eleven, twelve, thirteen, fourteen, fifteen, sixteen, seventeen, eighteen, or nineteen genomic regions selected from the group consisting of 2q31.2; 4q23; 7q22.3; 9q31.2; 9p21-p13; 9q34.3; 10q26.13; 12q13.2; 14q13.2; 15q24.1; 15q22.2; 16q13.13; 16q22.1; 16q22.2; 16q24.1; 16q24.2; 16p12.2; 16p12.3; and 21q22.13; wherein the contacting occurs under conditions to promote selective hybridization of the one or more nucleic acid probes to the three, four, five, six, seven, eight, nine, ten, eleven, twelve, thirteen, fourteen, fifteen, sixteen, seventeen, eighteen, or nineteen genomic regions. This is preferably accomplished using nucleic acid probes selected from the compositions of the various aspects and embodiments thereof disclosed above.

Any conditions, including hybridization reagents and wash conditions to remove unbound probe, in which the nucleic acid probes bind selectively to the target in the nucleic acid sample in the nucleic acid sample to form a hybridization complex, and minimally or not at all to other sequences, can be used in the methods of the present invention, as discussed above.

Any method for detecting formation of hybridization complexes and determining an alteration in gene copy number can be used, including but not limited to in situ hybridization (such as fluorescent in situ hybridization (FISH)), polymerase chain reaction (PCR) analysis, reverse transcription polymerase chain reaction (RT-PCR) analysis, Southern blotting, Northern blotting, array-based methods, and/or comparative genomic hybridization.

In a preferred embodiment, detection is performed by in situ hybridization ("ISH"). In situ hybridization assays are well known to those of skill in the art. Generally, in situ hybridization comprises the following major steps (see, for example, U.S. Pat. No. 6,664,057): (1) fixation of tissue, biological structure, or nucleic acid sample to be analyzed; (2) pre-hybridization treatment of the tissue, biological structure, or nucleic acid sample to increase accessibility of the nucleic acid sample (within the tissue or biological structure in those embodiments), and to reduce nonspecific binding; (3) hybridization of the probe to the nucleic acid sample; (4) post-hybridization washes to remove probe not bound in the hybridization and (5) detection of the hybridized nucleic acid fragments. The reagent used in each of these steps and their conditions for use varies depending on the particular application. In a particularly preferred embodiment, ISH is conducted according to methods disclosed in U.S. Pat. Nos. 5,750,340 and/or 6,022,689, incorporated by reference herein in their entirety.

In a typical in situ hybridization assay, cells are fixed to a solid support, typically a glass slide. The cells are typically denatured with heat or alkali and then contacted with a hybridization solution to permit annealing of labeled probes specific to the target nucleic acid sequence. The polynucleotides of the invention are typically labeled, as discussed above. In some applications it is necessary to block the hybridization capacity of repetitive sequences. In this case, human genomic DNA or Cot-1 DNA is used to block nonspecific hybridization.

In a further embodiment, an array-based format can be used in which the polynucleotides of the invention can be arrayed on a surface and the human nucleic sample is hybridized to the polynucleotides on the surface. In this type of format, large number of different hybridization reactions can be run essentially "in parallel." This provides rapid, essentially simultaneous, evaluation of a large number of nucleic acid probes. Methods of performing hybridization reactions in array based formats are also described in, for example, Pastinen (1997) Genome Res. 7:606-614; (1997) Jackson (1996) Nature Biotechnology 14:1685; Chee (1995) Science 274:610; WO 96/17958. Methods for immobilizing the polynucleotides on the surface and derivatizing the surface are known in the art; see, for example, U.S. Pat. No. 6,664,057, and are also described above.

In a sixth aspect, the present invention provides methods for classifying a glioma comprising:

(a) contacting a mRNA-derived nucleic acid sample obtained from a subject having a glioma with nucleic acid probes that, in total, selectively hybridize to two or more nucleic acid target sequences selected from the group consisting of SEQ ID NO:1-13 and 15-20 or their complements; wherein the contacting occurs under conditions to promote selective hybridization of the nucleic acid probes to the nucleic acid target sequences, or their complements, present in the nucleic acid sample;

(b) detecting formation of hybridization complexes between the nucleic acid probes to the nucleic acid target sequences, or their complements, wherein a number of such hybridization complexes provides a measure of gene expression of the one or more nucleic acid sequences according to SEQ ID NO:1-13 and 15-20; and (c) correlating a decrease in gene expression of the one or more nucleic acid sequences according to SEQ ID NO:1-13 and 15-20 relative to control with a classification of the glioma as an oligodendroglioma, and correlating a lack of increase in gene expression of the one or more nucleic acid sequences according to SEQ ID NO:1-13 and 15-20 relative to control with a classification of the glioma as a glioblastoma.

The method according to the sixth aspect of the invention detects changes in gene expression of one or more of the markers according to SEQ ID NO:1-13 and 15-20 relative to a control (for example, glioblastoma and/or oligodendroglioma standards), with a decrease in expression relative to control correlating with a classification of the glioma as a oligodendroglioma, and no increase in expression correlating with a classification of the glioma as an glioblastoma.

Thus, the methods of this aspect of the invention provide the ability to more accurately classify gliomas into oligodendrogliomas and glioblastomas, and provide information on glioma diagnosis, patient prognosis in the presence or absence of chemotherapy, a predicted optimal course for treatment of the patient, and patient life expectancy. For example, classification of the glioma as an oligodendroglioma indicates that the patient is more likely to respond to chemotherapy treatment then if the glioma was classified as a glioblastoma.

Thus, the invention further provides methods for treating a glioma patient, comprising carrying out the methods for classifying a glioma according to the different aspects and embodiments of the present invention, and then determining a course of treatment based on the results of the classification.

The mRNA-derived nucleic acid sample used in the methods of the present invention can be MRNA or cDNA derived from the mRNA. The nucleic acid sample used in the methods of the present invention can be from any source useful in characterizing a glioma, including but not limited to brain tissue samples (including but not limited to biopsies and solid tumor samples), cerebrospinal fluid, blood samples, (such as blood smears), and bone marrow cells, with special attention given to circulating tumor cells that have been shed from a tumor. The nucleic acid sample is preferably a cellular DNA or RNA sample, such as a sample prepared for in situ hybridization.

In various preferred embodiments of the methods of the sixth aspect of the invention, the nucleic acid probes are selected from the various aspects and embodiments of the compositions disclosed above, particularly the-third aspect of the invention and preferred embodiments thereof. In a most preferred embodiment, the polynucleotides of the probe sets comprise a detectable label, as disclosed above, and in particular the different probe sets comprise distinguishable detectable labels, to facilitate analysis of which genomic region(s) is/are the site of the altered copy number.

In various other preferred embodiments, the nucleic acid probes in total selectively hybridize to three, four, five, six, seven, eight, nine, ten, eleven, twelve, thirteen, fourteen, fifteen, sixteen, seventeen, eighteen, or nineteen different nucleic acid sequences according to SEQ ID NO:1-13 and 15-20 or their complements. Such probes according to this aspect of the invention can be of any length that permit selective hybridization under stringent conditions to the nucleic acid of interest, and preferably are at least 10 nucleotides in length. In various further embodiments, the probes according to this embodiment are at least 15, 20, 25, 30, 35, 40, 45, 50, 55, 60, 65, 70, 75, 80, 85, 90, 95, 100, 150, 200, 250, 300, 350, 400, 450, 500, 550, 600, 650, 700, 750, 800, 850, 900, 950, 1000 nucleotides in length. In a further embodiment, the probes according to this aspect of the invention are complementary to the entire deposited nucleic acid sequence as deposited under the recited accession numbers. The probes of this embodiment may be RNA or DNA and may be single or double stranded.

In a most preferred embodiment of this aspect, the nucleic acid probes comprise or consist of single stranded anti-sense polynucleotides of the nucleic acid compositions of the invention. For example, in mRNA fluorescence in situ hybridization (FISH) (ie. FISH to detect messenger RNA), only an anti-sense probe strand hybridizes to the single stranded mRNA in the RNA sample, and in that embodiment, the "sense" strand oligonucleotide can be used as a negative control.

Alternatively, DNA probes can be used as probes, preferably those according to the compositions of the invention. In this embodiment, it is preferable to distinguish between hybridization to cytoplasmic RNA and hybridization to nuclear DNA. There are two major criteria for making this distinction: (1) copy number differences between the types of targets (hundreds to thousands of copies of RNA vs. two copies of DNA) which will normally create significant differences in signal intensities and (2) clear morphological distinction between the cytoplasm (where hybridization to RNA targets would occur) and the nucleus will make signal location unambiguous. Thus, when using double stranded DNA probes, it is preferred that the method further comprises distinguishing the cytoplasm and nucleus in cells being analyzed within the bodily fluid sample. Such distinguishing can be accomplished by any means known in the art, such as by using a nuclear stain such as Hoechst 33342, or DAPI which delineate the nuclear DNA in the cells being analyzed. In this embodiment, it is preferred that the nuclear stain is distinguishable from the detectable probes. It is further preferred that the nuclear membrane be maintained, i.e., that all the Hoechst or DAPI stain be maintained in the visible structure of the nucleus.

Hybridization conditions and other details of the methods of this aspect are as described above for altered copy number analysis. In a preferred embodiment, RNA FISH is employed using standard methods in the art.

In each of the above aspects and embodiments, detection of hybridization is typically accomplished through the use of a detectable label on the nucleic acid probes, such as those described above. The label can be directly incorporated into the polynucleotide, or it can be attached to a molecule which hybridizes or binds to the polynucleotide. The labels may be coupled to the probes in a variety of means known to those of skill in the art, as described above. In a preferred embodiment, the detectable labels on the different probe sets of the compositions of the invention are distinguishable from each other, as discussed above. The label can be detectable can be by any techniques, including but not limited to spectroscopic, photochemical, biochemical, immunochemical, physical or chemical techniques, as discussed above.

In a further aspect, the present invention provides kits for use in the methods of the invention, comprising the compositions of the invention and instructions for their use. In a preferred embodiment, the probe sets are labeled, preferably so as to distinguish different probe sets, as disclosed above. In a further preferred embodiment, the probe sets are provided in solution, most preferably in a hybridization buffer to be used in the methods of the invention. In a further embodiment, the probe sets are provided on a solid support, such as those described above. In further embodiments, the kit also comprises wash solutions and/or pre-hybridization solutions.

EXAMPLES

Integrated Analysis of Disparate Data Types

The end aim of our analysis method is to identify significant DNA markers of disease stage or progression. We employ a method similar to meta-analysis, a technique for increasing statistical power by combining the results of independent but related studies. Conceptually, gene expression data and comparative genomic hybridization ("CGH") data analyses may be thought of as independent processes, followed by integration of the results. In practice, the analyses are conducted in parallel. The steps involved include:
  Mapping CGH band-resolution data to gene-resolution
  Search through putative markers for markers informative in both datasets
  Computation of significance of discovered markers Example Glioma Diagnostic Markers Background As a demonstration, we have analyzed publicly available microarray gene expression and CGH data collected from glioma tissue samples. The gene expression data was collected by Nutt et al (2003) in a study aimed at identifying patterns discriminative between high-grade oligodendroglioma and glioblastoma. CGH data for these two glioma subtypes, obtained from the Progenetix CGH data repository (www.progenetix.net), was originally collected in two independent studies by Kros et al (1999) and Maruno et al (1999). The microarray dataset consists of expression values for 12,558 genes measured across 22 oligodendroglioma and 28 glioblastoma samples. The CGH data, collected from 9 oligodendroglioma and 8 glioblastoma samples, consists of identified regions of gains and losses binned at a resolution of 862 cytogenetic bands.

Analysis of CGH Data without Gene Expression Data

Ideograms corresponding to the two CGH datasets were analyzed. The 862 bands contained in these datasets were ranked according to differential DNA content between the glioma subtypes as measured by t-scores. We employed a sample label permutation test (1000 permutations) to access the significance of these scores. Our analysis of only the CGH data did not identify statistically significant univariate marker bands indicative of glioma subtype, with the most significant band reaching a p-value of only 0.22. This lack of significance is the result of the common CGH data analysis situation wherein there are relatively few samples and low incidence of specific copy number aberrations.

Integrated Analysis of CGH and Gene Expression Data

Next we investigated whether the addition of gene expression information to the CGH data would enable the identification of significant markers. The initial step required by our technique is the mapping of the CGH data to the resolution of the gene expression data. Specific cytogenetic band mappings were available for 7583 of the microarray probes, and CGH data for each band was mapped to an artificial gene-scale resolution by transferring the data for each band to all genes within that band.

Following this preprocessing step, gene markers were evaluated using a combination of t-scores computed independently in the gene expression and CGH datasets. In this demonstration, the test statistic is simply the sum of the t-scores. The significance of these combined scores was again determined with a sample label permutation test (1000 permutations). Nineteen gene markers, located on 11 unique chromosome arms, were found to be significant (p=0.05). The significant genomic regions are detailed in FIG. 1, together with further information about the gene markers and genomic regions containing them.

Based on the above analysis, we have identified the following genes showing statistical significance (p<0.05) as glioma markers (ie: they tend to be present in decreased copy number in oligodendrogliomas relative to glioblastomas, and they tend to be expressed at a lower level in oligodendrogliomas relative to glioblastomas), based on the combined analysis of CGH and gene expression data:

Gen Bank Accession No. X68194:*H.sapiens* h-Sp1 MRNA (SEQ ID NO:1)

Gen Bank Accession No.D80012:Human MRNA for KIAA0190 gene (SEQ ID NO:2)

Gen Bank Accession No. X69490:*H.sapiens* MRNA for titin (SEQ ID NO:3)

Gen Bank Accession No. AL050050:*Homo sapiens* mRNA; cDNA DKFZp566D133 (from clone DKFZp566D133) (SEQ ID NO:4)

Gen Bank Accession No. Z35491 :*H.sapiens* mRNA for novel glucocorticoid receptor-associated protein (SEQ ID NO:5)

Gen Bank Accession No. AB029003:*Homo sapiens* mRNA for KIAA1080 protein (SEQ ID NO:6)

Gen Bank Accession No. D87343:*Homo sapiens* mRNA for DCRA (SEQ ID NO:7)

Gen Bank Accession No. X17644:Human GST1-Hs mRNA for GTP-binding protein (SEQ ID NO:8)

Gen Bank Accession No. D13642:Human mRNA for KIAA0017 gene (SEQ ID NO:9).

Gen Bank Accession No. M80244:Human E16 Mma (SEQ ID NO:10)

Gen Bank Accession No. M63175:Human autocrine motility factor receptor mRNA (SEQ ID NO:11)

Gen Bank Accession No. AJ009771:*Homo sapiens* mRNA for putative RING finger protein (SEQ ID NO:12)

Gen Bank Accession No. AB028985:*Homo sapiens* mRNA for KIAA1062 protein (SEQ ID NO:13)

Gen Bank Accession No. M81118:Human alcohol dehydrogenase chi polypeptide (ADH5) gene (SEQ ID NO:15)

Gen Bank Accession No. AF070596:*Homo sapiens* clone 24796 mRNA sequence (SEQ ID NO:16)

Gen Bank Accession No. AB018290:*Homo sapiens* MRNA for KIAA0747 protein (SEQ ID NO:17)

Gen Bank Accession No. AL050025:*Homo sapiens* mRNA; cDNA DKFZp564D066 (from clone DKFZp564D066) (SEQ ID NO:18)

Gen Bank Accession No. AC002394:Human Chromosome 16 BAC clone CIT987SK-A-211C6 (SEQ ID NO:19)

Gen Bank Accession No. AB 011170:*Homo sapiens* MRNA for KIAA0598 protein (SEQ ID NO:20)

While statistically significant, we believe that the clinical diagnostic utility of subsets of these nineteen gene markers will be greater than the clinical diagnostic utility of individual genes. Thus we investigated the potential diagnostic utility of 5 marker reporter sets of these nineteen gene markers. A genetic algorithm global search technique was employed to determine the most accurate 5 reporter set glioma biomarker from all possible 5 reporter set combinations within the 19 gene markers identified herein. The 50 most accurate combinations are presented in FIG. 2. This exemplary data confirms that probe sets consisting of 5 genes are highly diagnostic in both the gene expression data and CGH data.

REFERENCES

Crawley J J, Furge K A. Identification of frequent cytogenetic aberrations in hepatocellular carcinoma using gene-expression microarray data. Genome Biol. 2002; 3(12)

Hyman E, Kauraniemi P, Hautaniemi S, Wolf M, Mousses S, Rozenblum E, Ringner M, Sauter G, Monni O, Elkahloun A, Kallioniemi O P, Kallioniemi A. Impact of DNA amplification on gene expression patterns in breast cancer. Cancer Res.2002 Nov. 1; 62(21):6240-5.

Kros J M, van Run P R, Alers J C, Beverloo H B, van den Bent M J, Avezaat C J, van Dekken H. Genetic aberrations in oligodendroglial tumours: an analysis using comparative genomic hybridization (CGH). J Pathol. 1999Jul.; 188(3): 282-8.

Maruno M, Yoshimine T, Muhammad A K, Ninomiya H, Kato A, Hayakawa T. Chromosomal aberrations detected by comparative genomic hybridization (CGH) in human astrocytic tumors. Cancer Lett.1999 Jan. 8; 135(1):61-6.

Nutt C L, Mani D R, Betensky R A, Tamayo P, Cairncross J G, Ladd C, Pohl U, Hartmann C, McLaughlin M E, Batchelor T T, Black P M, von Deimling A, Pomeroy S L, Golub T R, Louis D N. Gene expression-based classification of malignant gliomas correlates better with survival than histological classification. Cancer Res.2003 Apr. 1; 63(7): 1602-7.

Pollack J R, Sorlie T, Perou C M, Rees C A, Jeffrey S S, Lonning P E, Tibshirani R, Botstein D, Borresen-Dale A L, Brown P O. Microarray analysis reveals a major direct role of DNA copy number alteration in the transcriptional program of human gliomas. Proc Natl Acad Sci USA.2002 Oct. 1; 99(20): 12963-8.

Progenetix CGH online database. Baudis M. (2000-2003): www.progenetix.net.

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US07534875B2). An electronic copy of the "Sequence Listing" will also be available from the USPTO upon request and payment of the fee set forth in 37 CFR 1.19(b)(3).

We claim:

1. An isolated composition consisting of between 3 and 47 different probe sets, wherein a first probe set consists of one or more probes consisting of 20 or more contiguous nucleotides of SEQ ID NO:3 or a full complement thereof and optionally a detectable label, a second probe set consists of one or more probes consisting of 20 or more contiguous nucleotides of SEQ ID NO:5 or a full complement thereof and optionally a detectable label, and a third probe set consists of one or more probes consisting of 20 or more contiguous nucleotides of SEQ ID NO:7 or a full complement thereof and optionally a detectable label, and wherein each of the between 3 and 47 different probe sets consists of one or more probes consisting of 20 or more contiguous nucleotides, or full complements thereof, of a single mRNA different from that of the other probe sets, and optionally a detectable label.

2. The isolated composition of claim 1 wherein the composition consists of between 4 and 47 different probe sets.

3. The isolated composition of claim 1 wherein the composition consists of between 5 and 47 different probe sets.

4. The isolated composition of claim 1 wherein the probes further comprise a detectable label.

5. The isolated composition of claim 1 wherein the composition consists of 3-23 different probe sets.

6. The isolated composition of claim 1, wherein the composition consists of 3-5 different probe sets.

7. The isolated composition of claim 4, wherein the detectable labels on the probes of one probe set are distinguishable from the detectable labels on the probes of the other probe sets.

8. The isolated composition of claim 1, wherein the first probe set consists of one or more probes consisting of 500 or more contiguous nucleotides of SEQ ID NO:3 or a full complement thereof, the second probe set consists of one or more probes consisting of 500 or more contiguous nucleotides of SEQ ID NO:5 or a full complement thereof, and the third probe set consists of one or more probes consisting of 500 or more contiguous nucleotides of SEQ ID NO: 7 or a full complement thereof.

9. The isolated composition of claim 5 wherein the probes further comprise a detectable label.

10. The isolated composition of claim 6 wherein the probes further comprise a detectable label.

11. The isolated composition of claim 9, wherein the detectable labels on the probes of one probe set are distinguishable from the detectable labels on the probes of the other probe sets.

12. The isolated composition of claim 10, wherein the detectable labels on the probes of one probe set are distinguishable from the detectable labels on the probes of the other probe sets.

13. The isolated composition of claim 8 wherein the probes further comprise a detectable label.

14. The isolated composition of claim 13, wherein the detectable labels on the probes of one probe set are distinguishable from the detectable labels on the probes of the other probe sets.

* * * * *